(12) United States Patent
Bravo Castillo

(10) Patent No.: US 8,679,192 B2
(45) Date of Patent: Mar. 25, 2014

(54) SYSTEM AND METHOD FOR ACQUIRING AND PROCESSING MYOELECTRIC SIGNALS IN ORDER TO CONTROL A PROSTHETIC ARM

(76) Inventor: Luis Armando Bravo Castillo, Tlalnepantla (MX)

( * ) Notice: Subject to any disclaimer, the term of this patent is extended or adjusted under 35 U.S.C. 154(b) by 0 days.

(21) Appl. No.: 13/393,886

(22) PCT Filed: Sep. 2, 2009

(86) PCT No.: PCT/MX2009/000093
§ 371 (c)(1), (2), (4) Date: May 21, 2012

(87) PCT Pub. No.: WO2011/028087
PCT Pub. Date: Mar. 10, 2011

(65) Prior Publication Data
US 2012/0232675 A1 Sep. 13, 2012

(51) Int. Cl.
*A61F 2/70* (2006.01)
(52) U.S. Cl.
USPC ................................ 623/25; 623/24; 623/57

(58) Field of Classification Search
USPC ................................. 623/25, 24, 57
See application file for complete search history.

*Primary Examiner* — Thomas J Sweet
*Assistant Examiner* — Matthew Schall
(74) *Attorney, Agent, or Firm* — Defillo & Associates, Inc; Evelyn A. Defillo

(57) ABSTRACT

The invention relates to a system for acquiring and processing myoelectric signals in order to control a prosthetic arm, comprising: a pair of electrodes positioned in a muscle in the residual limb of an arm that has been amputated in order to detect myoelectric signals; an electrode positioned at a distance from said pair of electrodes, which acts as an earth system; a myoelectric signal conditioning means; and a prosthesis controlling and processing means which receives conditioned signals from the conditioning means. According to the invention, the prosthesis controlling and processing means includes: a comparison means for comparing a muscle contraction time and a muscle contraction voltage with a threshold time and a threshold voltage, respectively; and an activation means for activating at least one motor which produces a predetermined movement of the prosthesis in response to an activation signal transmitted from the aforementioned comparison means. The electrodes provide the myoelectric signal for activating different movements of the prosthesis, without the electrodes having to be changed to another muscle.

19 Claims, 3 Drawing Sheets

SYSTEM AND METHOD FOR ACQUIRING AND PROCESSING MYOELECTRIC SIGNALS IN ORDER TO CONTROL A PROSTHETIC ARM

BACKGROUND AND FIELD OF THE INVENTION

The present invention relates with control of mechanical devices by means of electric signals produced by muscular contraction, and more particularly to a system and method for acquiring signals produced by muscular electrical activity at the outer surface level of the human epidermis, in order to control an arm prosthesis.

Nowadays, there are mechanical systems controlled by electric signals produced by muscular contraction, and can be find in many different applications. Electromechanical prosthesis responds in a precise way to the muscular stimulation of patients who have been lost a fractional of a superior member (either congenital or resulting from a surgery).

Conventional prosthetic arms working with corporal movements and depend of said corporal movements to manipulate wires that are controlling the prosthesis. Myoelectric prosthesis are controlled by electrical signals transmitted from inferior muscles to the epidermis, this signals are amplified and are sent to microprocessors that activate motors disposed in joints and hands If a muscle is contracted it produces an electrical signal due to depolarization of membranes of muscular fibers. Each cell gives a small voltage quantity, which together are converted in a sufficient significant signal so it can be captured by an electrode and thus be brought to a signals processing system.

As signal has a voltage level of a few millivolts, is necessary to make an electronic amplification in order to make any kind of processing, that it must be do in a similar way.

Any signal (particularly a biological signal) can be submitted to a huge variety of processing in order to obtain useful information from it, among which are: filtrated to remove unwanted frequency components, levels detection, determination of frequency spectrums, integration, derivation, among others. These processes can be carried out either analogically or digitally.

Given that digital systems are more adaptable and (many times) more efficient than analog systems, the employment of computers programs is the most appropriated.

There are many systems that can be used in order to produce movement like response to electric stimulus, such as, servomotors, stepper motors and direct current motors.

Generally in known systems are used different muscular areas in order to obtain any movement of the prosthesis, that is to say, it use readings of antagonist muscle contraction to make opposite movement, for example, open hand movement is carried on when there are biceps contraction, and close hand movement is carried on when there are triceps contraction, both are antagonist muscles, and carrying with the use of multiple electrodes.

In view of the above, is advantageous to have a myoelectric data acquisition system to control efficiently and simple the movements of a prosthesis, using a pair of electrodes to make the contraction readings, therefore is an objective of the invention provide a system for amplify, filtering and digitalizing myoelectric signals, in order to control an arm prosthesis, wherein is only used a pair of electrodes to detect signals to produce all the prosthesis movements.

Another objective of invention is to provide a system with many freedom degrees, capable of controlling the open and close hand movements, pronation and supination of forearm, flexion and extension of arm prosthesis.

Still another objective of the invention to provides a system that using muscular contraction time in order to controlling arm prosthesis movements.

The myoelectric data acquisition system and arm prosthesis control according present invention includes a pair of copper electrodes disposed on the best muscle area according patient amputation and a copper electrode away of said area, said electrode works like a biological ground. Due myoelectric signal is given in microvolts, it requires of amplification stage and conditioning of said signal in order to be processed and interpreted, so that a diversity of mechanicals movements are generated for the prosthesis according patient necessities in a simply and efficient way, only with alimentation of a 12 volts battery.

The system can be divided in two blocks, conditioning of myoelectric signal through operational amplifiers and analogue circuits, and digital control systems through a micro controller who has analog comparator, ND converter and drivers.

Invention provides a myoelectric data acquisition system in order to controlling an arm prosthesis, comprising: a pair of electrodes disposed in a muscle, in a residual piece of a person amputated arm, in order to detect myoelectric signals, and an electrode disposed in said residual arm piece, said electrode is move away of said pair electrodes and works like a ground, myiolectric signal conditioning means, and processing control prosthesis means which receive conditioned signals from conditioning means, wherein processing control prosthesis means: comparing means to evaluate muscular contraction time and muscular contraction voltage with threshold time and threshold voltage respectively activating means for activating at least a motor, said motor produce a predetermined movement of the prosthesis in response to an activation signal which is sent from comparing means, wherein the electrodes provides the myoelectric signal to activating different movements of the prosthesis, without changing electrodes to another muscle.

Activating means produces the activation of a motor to open a hand of the prosthesis, when the comparing means sends the activation signal, if the muscular contraction time is longer than the threshold time and the muscular contraction voltage is higher than the threshold voltage When the comparing means sends the activation signal, because the muscular contraction time is longer than the threshold time and the muscular contraction voltage is lower than the threshold voltage, activating means produces the activation of a motor to close the hand of the arm prosthesis. Activating means produces an activation motor to flex the arm prosthesis, when means to compare send the activation signal, if the muscular contraction time is lower than the threshold time, muscular contraction voltage is higher than the threshold voltage and the time between two muscular contractions is longer than 400 ms.

When comparing means sends an activation signal, due that the muscular contraction time is lower than the threshold time, the muscular contraction voltage is lower than the threshold voltage and the time between two muscular contractions is longer than 400 ms, activating means produces the activation of a motor to extend the arm prosthesis.

Activating means produces the activation of a motor for the pronation of a forearm prosthesis, when comparing means sends the activation signal, when comparing means sends the activation signal, if the muscular contraction time is lower than the threshold time, the muscular contraction voltage is higher than the threshold voltage and the time between two muscular contractions is lower than 400.

Activating means produces the activation of a motor for the supination of a forearm prosthesis, when comparing means sends the activation signal, if the muscular contraction time is lower than the threshold time, the muscular contraction voltage is lower than the threshold time and the time between two muscular contractions is shorter than 400 ms.

Also the invention provides a method of myoelectric acquisition and processing signals to control an arm prosthesis that consists in the following: detection of signals with a pair of electrodes placed in a muscle of a residual part of an arm that has been amputated of a person, and an electrode placed in a residual part of the arm away of the pair of electrodes functioning as ground; conditioning the signals to obtain a voltage value of muscular contraction; compare the muscular contraction time and the muscular contraction voltage with the threshold time and the threshold voltage, respectively; activating at least a motor to produce a predetermined prosthesis movement, in response to an activation signal; wherein to produce different movements of the prosthesis, the previous stages are repeated, without placing the electrodes in another muscle.

The activation of a motor to open a hand of the prosthesis, is produced when the comparing means sends the activation signal, if the muscular contraction time is longer than the threshold time and the muscular contraction voltage is higher than the threshold voltage.

The activation of a motor to close a hand of the prosthesis, is produced when the comparing means sends the activation signal, if the muscular contraction time is longer than the threshold time and the muscular contraction voltage is lower than the threshold voltage.

The activation of a motor to flex the arm prosthesis, is produced when the means to compare sends the activation signal, if the muscular contraction time is shorter than the threshold time, the muscular contraction voltage is higher than the threshold voltage and the time between two muscular contractions is longer than 400 ms.

the activation of a motor to extend the arm prosthesis is produced, when the means to compare sends the activation signal, if the muscular contraction time is shorter than the threshold time, the muscular contraction voltage is lower than the threshold voltage and the time between two muscular contractions is longer than 400 ms.

The activation of a motor for the pronation of a forearm of the prosthesis, is produced when the means to compare sends the activation signal, if the muscular contraction time is shorter than the threshold time, the muscular contraction voltage is higher than the threshold voltage and the time between two muscular contractions is shorter than 400 ms.

The activation of a motor for a supination of a forearm of the prosthesis, is produced when the means to compare sends the activation signal, if the muscular contraction time is shorter than the threshold time, the muscular contraction voltage is lower than the threshold voltage and the time between two muscular contractions is shorter than 400 ms.

BRIEF DESCRIPTION OF THE DRAWINGS

To have a better understanding of the invention is provided a description thereof, together with the accompanying drawings, in which:

The FIG. 1 is a blocks diagram of the acquisition system of myoelectric data in accordance with the present invention;

Figure 2:
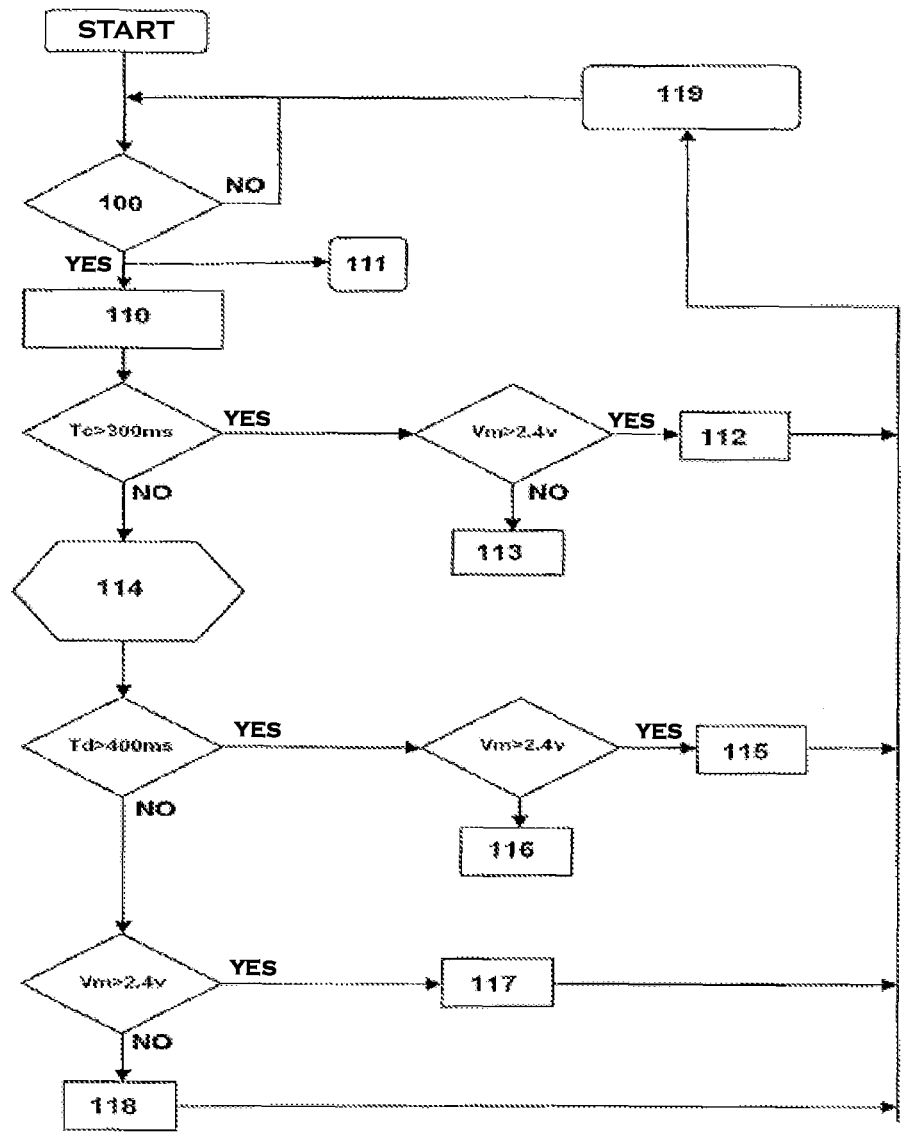
Figure 3A:
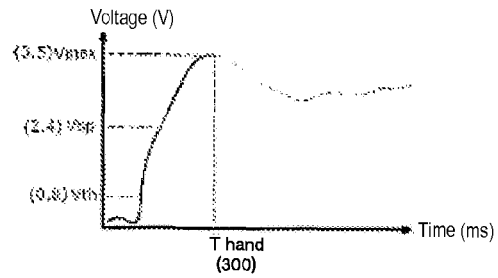
Figure 3B:
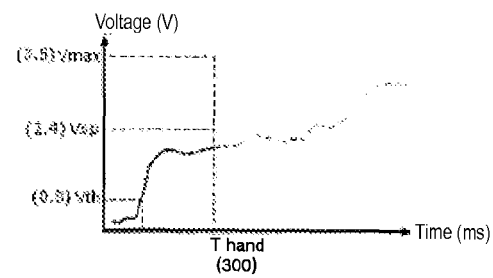
Figure 4A:
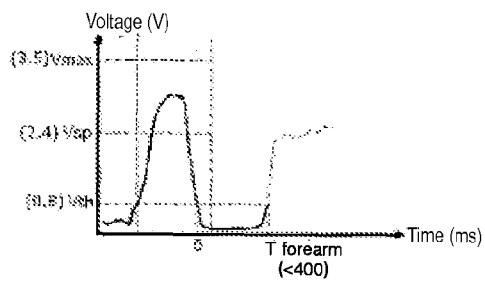
Figure 4B:
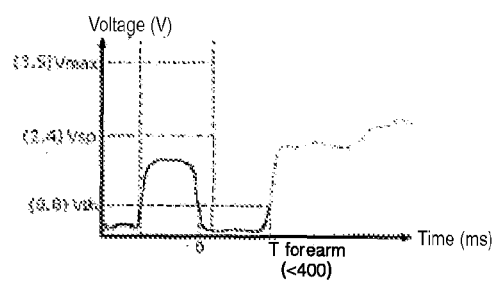
Figure 5A:
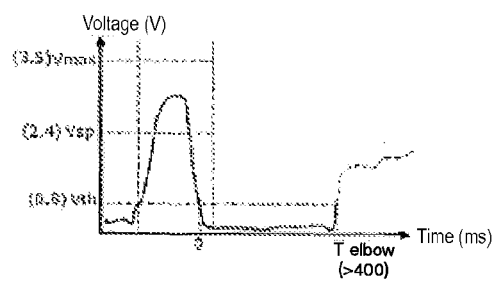
Figure 5B:
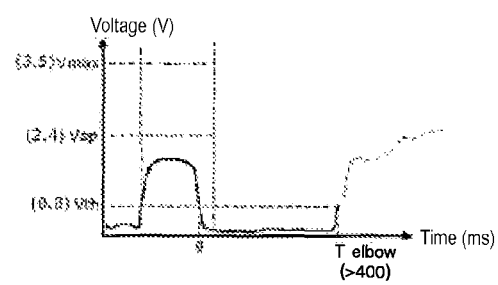

The FIG. 2 is a flowchart of the control system in accordance with the present invention;

The FIGS. 3a and 3b are graphics that show the signals obtained with contractions to open and close the hand;

The FIGS. 4a and 4b are graphics that show the signals obtained with contractions for the pronation and supination of the forearm; and The FIGS. 5a and 5b are graphics that show the signals obtained with contractions for the flexion and extension of the arm.

DETAILED DESCRIPTION OF THE INVENTION

In order to control an arm prosthesis, from the obtained electric signals produced by the muscular tissue to the electrodes, is indispensable to condition electrically those signals in a manner that a microprocessor could be able to coordinate a controller instructed by the patient and the movements of the motors of the arm prosthesis.

Figure 1:
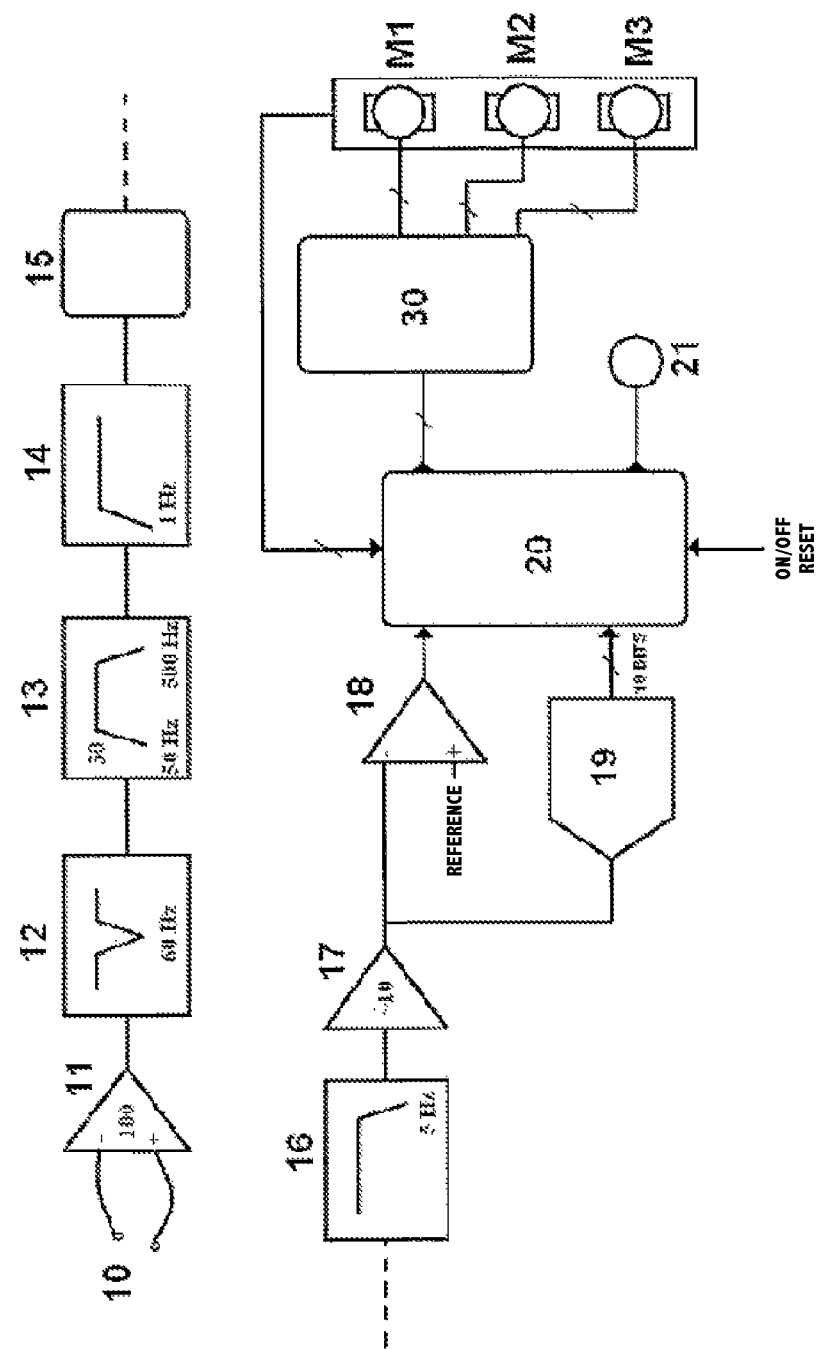

In reference to the FIG. 1, a myoelectric signal from the electrodes (10) passes into a first stage constituted by an Amplifier of Instrumentation (11) with a gain of 100 which registers and amplifies the myoelectric signal.

The second stage consists in a Filter (12) Suppressor of 60 Hz that filters the electromagnetic residual energy captured for the human body from the electric infrastructure that operates in 60 Hz through a Band-Stop filter (Notch filter).

The third stage is a filter Band-Pass (13) due to the myoelectric signals that present a frequency spectrum between 50 Hz and 5 Khz from which the largest amount of energy is located between the 50 and 500 Hz. In consequence, it's used an amplifier with a band width of 100 Hz and 500 Hz, the filter is a Butterworth filter of the $2^{nd}$ order. The lower frequency has been chosen taking in mind the elimination of the noise of 60 Hz and the higher frequency was limited to 500 Hz to avoid that the frequency of the motors operation (6 KH) could infer with the system.

The fourth stage is a (DC) Constant Voltage Filter (14), which removes an undesirable Offset level for the RMS conversion to DC since it would be presented a residual constant level in the myoelectric conditioner outlet. This filter (14) also contributes in the intensity reduction of the cardiac signal and the component of 60 Hz.

The fifth stage has an RMS converter (15) to DC that obtains the intensity with which the muscles contract, from the value RMS of the myoelectric signal.

The sixth stage consists in the Softening and Amplification of the Myoelectric Intensity Signal that avoids a wrong operation of the control system, through a Low-Pass filter (16) and a Non-Inverting Amplifier (17)

The control system stage has a microcontroller (20), which is in charge of coordinating the movements of the prosthesis in function of a program and a myoelectric signal. The obtained signal of the non-inverting amplifier (17) is fed to the microcontroller (20) trough a comparator (18) and a digital analog converter (19). The microcontroller (20) also activates a gadget (21) of a feedback learning (buzzer) which emits a sound for the patient or user that indicates the contraction intensity. The microcontroller (18) can be the PIC16F88 produced by Microchip, or the MSP430eZ430 of the Texas Instruments.

The motor potential stage (30) is controlled by two controllers (Drivers), said controllers gives sufficient energy according patient requirements, and by stopped sensors which limiting the motor twist M1-M3 to a determinate movement period.

The digital control system contains a program whereby recognize prepared myoelectric signal and is given the prosthesis control to the patient through his contraction muscles.

Said contraction are administrated by threshold such that contraction voltage intensity is less 0.8 volts (Vth) is considered like a null. If said contraction voltage falls within the range of 0.8 to 2.4 volts is considered like a weak contraction and if it is higher than 2.4 volts (Vsp) is considered strong contraction, said thresholds can oscillate according to physics characteristics of each patient.

With reference to flowchart of the FIG. 2, we have the process (100) begins asking if exist muscular contraction, if do not exist, return to ask to detect muscular contraction.

If exist muscular contraction, the contraction time and voltage intensity (110) are measured and a sound is emitted.

Later, if muscular contraction is for a time higher of 300 ms (contraction time), and intensity voltage higher to 2.4 volts, the motor (112) is activated to open the hand (FIG. 3A). If muscular contraction is for higher time to 300 ms and voltage intensity is less than 2.4 volts, the motor (113) is activated to close the hand (FIG. 3B).

When the contraction time is less to 300 ms, is hoped a second contraction and the time Td to take place said second contraction, is measured (114).

If the muscle is relaxed after the first contraction in a less time Td to 400 ms, before to return to contracting the muscle, and the voltage intensity of said first contraction is higher than 2.4 volts, the forearm pronation motor (117) is activated in order to place the hand palm downward (FIG. 4A).

If the muscle is relaxed after the first contraction in a less time Td to 400 ms, before to return to contracting the muscle, and the voltage intensity of said first contraction is less than 2.4 volts, the forearm supination motor (118) is activated in order to place the hand palm upward (FIG. 4B).

If the muscle is relaxed after the first contraction in a higher time (Td) to 400 ms, before to return to contracting the muscle, and the voltage intensity of said first contraction is higher than 2.4 volts, the motor (115) is activated in order to do an arm bending (FIG. 5A).

If the muscle is relaxed after the first contraction in a higher time (Td) to 400 ms, before to return to contracting the muscle, and the voltage intensity of said first contraction is less than 2.4 volts, the motor (116) is activated in order to do an arm extension (FIG. 5B).

After activating any arm movement, the velocity can be controlled through the intensity with which the muscle is contracted, to higher contraction a higher velocity. Power supply to myoelectric intensity signal conditioner circuit has a +9 volts positive voltage regulator and −9 volts negative voltage regulator.

Digital control system supply is obtained through a 5 volts regulator.

With a 12 volts battery are supplied the controllers (drivers) which in turn modulate necessary energy to the motors (hand, beforehand, elbow) according patient demand.

Present invention has been described and illustrated according to a preferred embodiment, however, it will be obvious for an expert in the art, to do a multiplicity of changes and modifications of this invention, for example, can be varied time values and threshold voltage in order to adjust it to the physical characteristics of each patient, and to do a lot of combinations achieving activating a higher number of motors, without divert or move away of scope of next claims.

The invention claimed is:

1. A myoelectric data acquisition system for controlling an arm prosthesis comprising:
a first and a second electrodes adapted to be placed in a muscle in a residual piece of a person's amputated arm, the first and the second electrodes detect myoelectric signals,
a third electrode adapted to be placed away from said residual piece of the person's amputated arm, said third electrode is placed a distance away from said first and second of electrodes, the third electrode functions a ground,
a conditioning device to condition the myoelectric signals, and
a control and processing device to receive the conditioned signals from the conditioning device,
wherein the control and processing device includes:
a comparing device for evaluating a muscular contraction time by using a threshold time and a muscular contraction voltage by using a threshold voltage
an activating device for activating at least one motor, said motor producing a predetermined movement of the arm prosthesis in response to an activation signal which is sent from the comparing device,
wherein the system uses the muscular contraction time in order to control different arm prosthesis movements;
wherein the different arm prosthesis movements are made performed without changing the first and the second electrodes to another muscle;
wherein the movement of the arm prosthesis includes opening of a hand of the prosthesis, a closing of the hand of the prosthesis, pronation of a forearm of the prosthesis, supination of the forearm prosthesis, flexion of the arm prosthesis, and extension of the arm prosthesis.

2. The system according to claim 1, wherein the conditioning device includes a frequency filter before a band-pass filter with an amplifier with a broadband frequency range of approximately 100 to 500 Hz.

3. The system according to claim 1, wherein the threshold time is approximately 300 ms and the threshold voltage is approximately 2.4 volts.

4. The system according to claim 1, wherein if the muscular contraction time is longer than the threshold time and the muscular contraction voltage is higher than the threshold voltage, the activation device activates the at least one motor to open the hand of the prosthesis when the comparing device sends the activation signal.

5. The system according to claim 1, wherein if the muscular contraction time is longer than the threshold time and the muscular contraction voltage is lower than the threshold voltage, the activation device activates the at least one motor to close the hand of the prosthesis when the comparing device sends the activation signal.

6. The system according to claim 1, wherein, if the muscular contraction time is shorter than the threshold time, the muscular contraction voltage is higher than the threshold voltage and the time between two muscular contractions is longer than approximately 400 ms, the activation device activates the at least one motor to flex the arm prosthesis when the comparing device sends the activation signal.

7. The system according to claim 1, wherein if the muscular contraction time is shorter than the threshold time, the muscular contraction voltage is lower than the threshold voltage and the time between two muscular contractions is longer than approximately 400 ms, the activation device activates the at least one motor to extend the arm prosthesis when the comparing device sends the activation signal.

8. The system according to claim 1, wherein if the muscular contraction time is shorter than the threshold time, the muscular contraction voltage is higher than the threshold voltage and the time between two muscular contractions is shorter than approximately 400 ms, the activation device activates the at least one motor for the pronation of a forearm of the arm prosthesis when the comparing device sends the activation signal.

9. The system according to claim 1, wherein if the muscular contraction time is shorter than the threshold time, the muscular contraction voltage is lower than the threshold time and the time between two muscular contractions is shorter than approximately 400 ms, the activation device activates the at least one motor for the supination of a forearm of the arm prosthesis when the comparing device sends the activation signal.

10. The system according to claim 1, wherein the conditioning device includes a 9 volt positive voltage regulator and 9 volt negative voltage regulator and the control and processing device includes a 5 volt regulator.

11. A method of acquiring and processing myoelectric signals to control an arm prosthesis, said arm prosthesis adapted to be attached to a residual part of an arm, the method including the steps of:
   detecting signals from a first and a second electrodes, said first and said second electrodes adapted to be placed in a muscle of said residual part of the arm, a third electrode adapted to be placed in the residual part of the arm, the third electrode placed a distance away from the first and the second electrodes, the third electrode functions as a ground;
   conditioning the signals to obtain a voltage value of a muscular contraction;
   determining a contraction time and a contraction voltage;
   comparing the muscular contraction time with a threshold time and the muscular contraction voltage with a threshold voltage;
   activating at least one motor to produce a predetermined prosthesis movement in response to an activation signal;
   optionally repeating the detecting, conditioning, determining, comparing and activation steps without placing the electrodes in another muscle to produce different movements of the prosthesis,
   wherein the system uses the muscular contraction time in order to control different arm prosthesis movements;
   wherein the movement of the arm prosthesis includes opening of a hand of the prosthesis, a closing of the hand of the prosthesis, pronation of a forearm of the prosthesis, supination of the forearm prosthesis, flexion of the arm prosthesis, and extension of the arm prosthesis.

12. The method according to claim 11, wherein the conditioning step includes filtering approximately 60 Hz of myoelectric signal frequency.

13. The method according to claim 11, wherein the threshold time is approximately 300 ms and the threshold voltage is approximately 2.4 volts.

14. The method according to claim 11, wherein if the muscular contraction time is longer than the threshold time and the muscular contraction voltage is higher than the threshold voltage, the at least one motor is activated to open a hand of the prosthesis in response to the activation signal.

15. The method according to claim 11, wherein if the muscular contraction time is longer than the threshold time and the muscular contraction voltage is lower than the threshold voltage, the at least one motor is activated to close a hand of the prosthesis in response to the activation signal.

16. The method according to claim 11, wherein if the muscular contraction time is shorter than the threshold time, the muscular contraction voltage is higher than the threshold voltage and the time between two muscular contractions is longer than approximately 400 ms, the at least one motor is activated to flex the arm prosthesis in response to the activation signal.

17. The method according to claim 11, wherein if the muscular contraction time is shorter than the threshold time, the muscular contraction voltage is lower than the threshold voltage and the time between two muscular contractions is longer than approximately 400 ms, the at least one motor is activated to extend the arm prosthesis in response to the activation signal.

18. The method according to claim 11, wherein if the muscular contraction time is shorter than the threshold time, the muscular contraction voltage is higher than the threshold voltage and the time between two muscular contractions is shorter than approximately 400 ms, the at least one motor is activated for the pronation of a forearm of the prosthesis in response to the activation signal.

19. The method according to claim 11, wherein if the muscular contraction time is shorter than the threshold time, the muscular contraction voltage is lower than the threshold voltage and the time between two muscular contractions is shorter than approximately 400 ms, the at least one motor is activated for a supination of a forearm of the prosthesis in response to the activation signal.

* * * * *